(12) United States Patent
Reimers

(10) Patent No.: US 7,872,163 B1
(45) Date of Patent: Jan. 18, 2011

(54) PROCESS FOR PRODUCTION OF 3,4-DICHLOROBUTENE-1

(75) Inventor: Jay Reimers, Geismar, LA (US)

(73) Assignee: DuPont Performance Elastomers L.L.C., Wilmington, DE (US)

( * ) Notice: Subject to any disclaimer, the term of this patent is extended or adjusted under 35 U.S.C. 154(b) by 0 days.

(21) Appl. No.: 12/639,570

(22) Filed: Dec. 16, 2009

(51) Int. Cl.
*C07C 17/00* (2006.01)
(52) U.S. Cl. ..................................... 570/236
(58) Field of Classification Search .................. 570/236
See application file for complete search history.

(56) References Cited

U.S. PATENT DOCUMENTS

| | | | |
|---|---|---|---|
| 2,242,084 A | 5/1941 | Nicodemus et al. | |
| 3,819,730 A | 6/1974 | Nakata et al. | |
| 4,827,059 A | 5/1989 | Harris et al. | |
| 5,237,114 A | 8/1993 | Englert, Jr. et al. | |
| 6,380,446 B1 | 4/2002 | Drew et al. | |
| 6,392,107 B2 | 5/2002 | Schertl | |

OTHER PUBLICATIONS

G. Henrici-Olive and S. Olive, Kinetics and Mechanism of the Iron Catalyzed Positional Isomerization of Dichlorobutenes, J. Organometal. Chem. 1971, 301-311, 29, Elsevier Sequoia, S.A., Lausanna, The Netherlands.

C.A. Stewart, Jr., et al., Chloroprene Polymers, Encyclopedia of Polymer Science and Engineering, 1985, 441-462, vol. 3, John Wiley & Sons, Inc.

*Primary Examiner*—Jafar Parsa
(74) *Attorney, Agent, or Firm*—Marilyn H. Bromels

(57) ABSTRACT

3,4-Dichlorobutene-1 is produced by a process comprising the step of contacting 1,4-dichlorobutene-2 with either 1) a ferric carboxylate catalyst of the formula

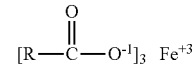

where R is an alkyl or alkenyl group of 4-18 carbon atoms, a cycloalkyl or cycloalkenyl group of 6-18 carbon atoms or an aryl group selected from phenyl, benzyl, xylyl, tolyl, and naphthyl groups, whereby a portion of the 1,4-dichlorobutene-2 is isomerized to form 3,4-dichlorobutene-1, or 2) a ferric carboxylate catalyst of the formula

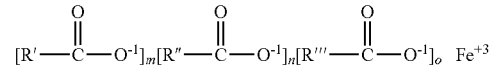

where R, R' and R" are independently alkyl or alkenyl groups of 4-18 carbon atoms, cycloalkyl or cycloalkenyl groups of 6-18 carbon atoms or aryl groups selected from phenyl, benzyl, xylyl, tolyl, and naphthyl groups, the sum of m, n and o is 3 and m, n and o are independently 0, 1 or 2, whereby a portion of the 1,4-dichlorobutene-2 is isomerized to form 3,4-dichlorobutene-1.

7 Claims, No Drawings

PROCESS FOR PRODUCTION OF 3,4-DICHLOROBUTENE-1

FIELD OF THE INVENTION

This invention relates to a process for producing 3,4-dichlorobutene-1 by isomerization of 1,4-dichlorobutene-2 in the presence of an iron catalyst.

BACKGROUND OF THE INVENTION 2-chlorobutadiene-1,3 ("chloroprene") is an important monomer used in the commercial manufacture of a number of synthetic chloroelastomers. Chloroprene may be produced from olefins using well-known multi-step processes that involve a series of chlorination and dehydrochlorination reactions of olefins. Such processes are disclosed in general in C. A. Stewart, Jr. et al., *Chloroprene Polymers*, in Encyclopedia of Polymer Science and Engineering, Vol. 3 (Second Ed), John Wiley and Sons (1965), 441-462. In one important commercial process butadiene is reacted with chlorine to form a mixture of 1,4-dichlorobutene-2 and 3,4-dichlorobutene-1. The mixture is then isomerized to increase the concentration of 3,4-dichlorobutene-1 and the resultant product is dehydrochlorinated, generally in the presence of aqueous alkali, to yield chloroprene monomer. Examples of such isomerization and dehydrochlorination processes are described, for example in U.S. Pat. Nos. 3,819,730; 4,827,059; 5,237,114; and 6,380,446.

The isomerization step may be conducted in the presence of copper salts and complexes, e.g. in the presence of a complex of a copper salt with a quaternary ammonium compound, as described in U.S. Pat. No. 3,819,730. An improvement to this process is disclosed in U.S. Pat. No. 4,827,059, wherein the isomerization is conducted in the presence of a hydroxylamine for the purpose of reducing formation of by-products. A disadvantage of using copper complex catalysts in the isomerization reaction is that when the isomerization is operated at low temperatures, e.g. below about 90° C., low conversions are achieved. Conversely, when the isomerization is conducted at high temperatures in the presence of copper complex catalysts, excessive amounts of by-products, for example, oligomerized and/or polymerized materials, are formed. This adversely affects efficiency and yield of the desired product.

It is also known to use other transition metal catalysts in isomerization reactions of dichlorobutenes. For example, the use of iron compounds and complexes as catalysts for the isomerization reactions of chlorobutenes is known. U.S. Pat. No. 2,242,084 discloses isomerization of 3,4-dichlorobutene-1 to 1,4-dichlorobutene-2 using iron chloride. U.S. Pat. No. 6,392,107 discloses the use of iron metallocene compounds having cyclopentadienyl and substituted cyclopentadienyl groups as catalysts for the isomerization reaction. In addition, the use of iron acetylacetonate to catalyze isomerization of dichlorobutenes is disclosed in G. Henrici-Olive and S. Olive, *Kinetics and Mechanism of the Iron Catalyzed Positional Isomerization of Dichlorobutenes*, J. Organometal. Chem., 29 (1971) 307-311. A disadvantage of both of these catalysts is that they are costly and contain ligands that are highly basic and easily protonated. Protonation results in some degree of catalyst decomposition which leads to deactivation and insolubility in the reaction media.

It would be desirable to have available alternative catalysts suitable for use in dichlorobutene isomerization that are capable of low byproduct formation and can be used at low levels but which are not associated with these disadvantages.

SUMMARY OF THE INVENTION

The present invention is directed to a process for producing 3,4-dichlorobutene-1 comprising the step of contacting 1,4-dichlorobutene-2 with a ferric carboxylate catalyst of the formula

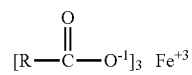

where R is $C_4$-$C_{18}$ alkyl, $C_4$-$C_{18}$ alkenyl, $C_6$-$C_{18}$ cycloalkyl, $C_6$-$C_{18}$ cycloalkenyl, phenyl, benzyl, xylyl, tolyl, or naphthyl, whereby a portion of the 1,4-dichlorobutene-2 is isomerized to form 3,4-dichlorobutene-1.

DETAILED DESCRIPTION OF THE INVENTION

The present invention relates to a process for isomerizing dichlorobutenes in the presence of a ferric carboxylate salt catalyst that permits isomerization of the dichlorobutenes to proceed rapidly and in high yield, while producing low levels of by-products.

The ferric salt catalyst is a composition of the formula

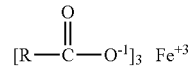

where R is an alkyl or alkenyl group of 4-18 carbon atoms, a cycloalkyl or cycloalkenyl group of 6-18 carbon atoms or an aryl group selected from aryl groups including phenyl, benzyl, xylyl, tolyl, and naphthyl groups. The alkyl, cycloalkyl, alkenyl or cycloalkenyl groups may bear alkyl substituent groups, such as methyl and ethyl groups. Thus, the R group may be a linear or branched alkyl radical or it may be a cycloalkyl or cycloalkenyl radical that is substituted with linear or branched groups. The catalyst is a ferric carboxylate salt. Examples of suitable ferric carboxylates include iron (III) 2-ethylhexanoate, iron (III) octanoate, iron (IIII) propionate, iron (III) butyrate, iron (III) benzoate, iron (III) naphthenate, iron (III) stearate, iron (III) oleate, and iron (III) cyclohexanoate. Preferred salts include those wherein the conjugate acid of the salt has a boiling point above 160° C. at atmospheric pressure. Most preferred salts include iron (III) 2-ethylhexanoate and iron (III) naphthenate.

The carboxylate residues may be the same or different. For example, the ferric salt may be a mixed salt of the type

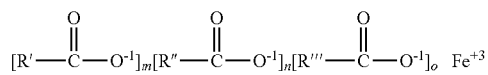

where the sum of m, n and o is 3 and m, n and o are independently 0, 1 or 2. Examples of such mixed salts include iron (III) 2-ethylhexanoate, iron (III) n-octanoate, iron (III) oleate and iron (III) stearate.

The isomerization process may be conducted by heating the dichlorobutene to be isomerized in the presence of the iron (III) carboxylate catalyst, generally in the absence of water and with substantial exclusion of air at a temperature at which the system is homogeneous, and removing the isomerized product from the reaction medium. By substantial exclusion of air is meant that less than 100 ppm of oxygen is present based on the total weight of the reactor contents.

The process of the invention may be utilized to produce a product that contains a major proportion of 3,4-dichlorobutene-1, which is an intermediate useful in the manufacture of chloroprene monomer. By major proportion is meant at least 15 wt. % 3,4-dichlorobutene-1, based on the total weight of dichlorobutenes present in the composition.

The amount of catalyst present will normally be from 0.01-1.0 weight percent, based on the weight of dichlorobutenes present, i.e. the total weight of dichlorobutene isomers to be isomerized. Preferably, the amount of catalyst utilized will be 0.02-0.50 weight percent, based on the weight of dichlorobutenes present. Optimum results are obtained when the amount of catalyst is such that the weight percentage of iron is about 0.05-0.20 weight percent of the weight dichlorobutenes present in the reactor. Below 0.02 weight percent, the rate of isomerization may be too low for a commercially attractive operation, although successful isomerizations can be carried out even when the amount of catalyst is reduced to about 0.01 wt. % iron. At levels above 1.00 wt. %, corrosion problems and spontaneous decomposition can occur.

This isomerization reaction may be a continuous or batch reaction. The reaction will produce an equilibrium mixture of the two isomers, i.e. 1,4-dichlorobutene-2 and 3,4-dichlorobutene-1. The percentage of each isomer will be the equilibrium mixture at the particular reaction conditions. It is preferred to operate the process continuously. The process will normally be conducted at a reduced pressure such that the reaction medium is at its boiling temperature and the product can be removed therefrom. Normally, the pressure will be about 100 torr (13.3 MPa), 350 torr (46.7 MPa), or preferably about 200 torr (26.7 MPa)-300 torr (39.9 MPa) and the temperature will be about 60° C.-120° C., preferably about 105° C.-115° C.

The process may be conducted by supplying 1,4-dichlorobutene-2 or 3,4-dichlorobutene-1 or a mixture of the chlorinated butenes to a constant boiling reactor operating under reduced pressure and containing the iron (III) carboxylate salt catalyst. The isomerized dichlorobutene product, which will be a mixture of 1,4 and 3,4 isomers, is removed as a vapor, then condensed and fractionally distilled to yield substantially pure 3,4-dichlorobutene-1 and 1,4-dichlorobutene-2, respectively. The reaction products may be detected and analyzed by gas chromatography.

A characteristic of the process of the present invention is that the catalyst is long-lived and does not degrade quickly to form iron chloride. The process is therefore efficient and cost effective. In particular, conversions do not decrease due to formation of iron chloride.

The products of the isomerization reaction, i.e. 3,4-dichlorobutene-1 or 1,4-dichlorobutene-2, are useful as intermediates in the manufacture of chloroprene, which may subsequently be used to manufacture polychloroprene elastomers. For example, in the preparation of polychloroprene, 3,4-dichlorobutene-1 is dehydrochlorinated to form chloroprene monomer which is subsequently polymerized to form polychloroprene. The products of the isomerization reaction are also useful in the manufacture of polyamides.

The invention is illustrated by the following examples of certain embodiments.

EXAMPLES

Example 1

A continuous isomerization unit consisting of a nitrogen-swept 1 liter reaction flask equipped with reflux condenser, metering feed pump, cold trap, vacuum pump, thermometer, stirrer, and sample collection bottle was used. A catalyst solution of iron (III) 2-ethylhexanoate in mineral spirits, having an iron content of 6 wt. %, available from The Shepherd Chemical Co., was used without further purification. A 1.86 g sample of the catalyst solution was added to 500 ml of 1,4-dichlorobutene-2 (0.04 mmol of iron catalyst per liter of solution) heated to a temperature of 110° C. in the continuous reactor. The pressure was held constant at 275 torr and sufficient heat was applied to boil 5 ml/minute overhead, where the product was condensed and collected. The level was held constant in the reactor by feeding 5 ml/minute of 1,4-dichlorobutene-2 to the reactor with a metering pump. The overhead stream, which contained a mixture of 1,4-dichloro-butene-2 and 3,4-dichlorobutene-1 was continuously removed and then separated by distillation.

TABLE I

| Turnovers[1] | Percentage 3,4-Dichlorobutene-1 in Distillate |
|---|---|
| 1 | 48 |
| 10 | 43 |
| 20 | 37 |
| 30 | 28 |

[1]t/T, where T is the residence time, (V/Q), the reactor volume divided by the volumetric flow rate to the reactor.

Comparative Example 1

Using the same continuous isomerization unit as described in Example 1, 0.71 g of iron (III) acetylacetonate (Sigma-Aldrich) was added to 500 ml of 1,4-dichlorobutene-1 (0.04 mmol of iron catalyst per liter of solution) heated to 110° C. in the continuous reactor. The pressure was held constant at 275 torr and sufficient heat was applied to boil 5 ml/minute overhead, where the product was condensed and collected. The level was held constant in the reactor by feeding 5 ml/minute of 1,4-dichlorobutene-1 to the reactor with a metering pump. The overhead stream which contained a mixture of 1,4-dichloro-2-butene and 3,4-dichloro-1-butene was continuously removed and monitored for composition over set lengths of runtime, as measured in Turnovers. The runtimes represent the time during which the reactor was heated and may not be continuous.

TABLE II

| Turnovers | Percent 3,4-Dichlorobutene-1 in the Distillate |
|---|---|
| 1 | 41 |
| 10 | 37 |
| 20 | 18 |
| 30 | 10 |

Comparative Example 2

Using the same continuous isomerization unit, 0.32 g of iron (III) chloride (Sigma-Aldrich) was added to 500 ml of 1,4-dichlorobutene-1 (0.04 mmol of iron catalyst per liter of solution) heated to 110° C. in the continuous reactor. The pressure was held constant at 275 torr and sufficient heat was applied to boil 5 ml/minute overhead, where the product was condensed and collected. The level was held constant in the reactor by feeding 5 ml/minute of 1,4-dichlorobutene-2 to the reactor with a metering pump. The overhead stream which contained a mixture of 1,4-dichloro-2-butene and 3,4-dichloro-1-butene was continuously removed and monitored for composition over set lengths of runtime, as measured in Turnovers. The runtimes represent the time during which the reactor was heated and may not be continuous.

TABLE III

| Residence Times (dim) | Percent 3,4-Dichlorobutene-1 in the Distillate |
|---|---|
| 1 | 6 |
| 10 | 8 |
| 20 | 8 |
| 30 | 8 |

Example 2

Using the same continuous isomerization unit, 2 ml of a 1M iron (III) ethoxide in ethanol (Sigma-Aldrich) was added to 500 ml of 1,4-dichlorobutene-2 (0.04 mmol of iron catalyst per liter of solution) heated to 110° C. in the continuous reactor. The pressure was held constant at 275 torr and sufficient heat was applied to boil 5 ml/minute overhead, where the product was condensed and collected. The level was held constant in the reactor by feeding 5 ml/minute of 1,4-dichlorobutene-2 to the reactor with a metering pump. The overhead stream which contained a mixture of 1,4-dichloro-2-butene and 3,4-dichloro-1-butene was continuously removed and monitored for composition over set lengths of runtime, as measured in Turnovers. The runtimes represent the time during which the reactor was heated and may not be continuous.

TABLE IV

| Turnovers | Percent 3,4-Dichlorobutene-1 in the Distillate |
|---|---|
| 1 | 21 |
| 10 | 15 |
| 20 | 12 |
| 30 | 8 |

What is claimed is:

1. A process for producing 3,4-dichlorobutene-1 comprising the step of contacting 1,4-dichlorobutene-2 with a ferric carboxylate catalyst of the formula

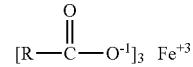

where R is an alkyl or alkenyl group of 4-18 carbon atoms, a cycloalkyl or cycloalkenyl group of 6-18 carbon atoms or an aryl group selected from phenyl, benzyl, xylyl, tolyl, and naphthyl groups, whereby a portion of the 1,4-dichlorobutene-2 is isomerized to form 3,4-dichlorobutene-1.

2. A process of claim 1 wherein R is an alkyl group of 4-18 carbon atoms.

3. A process of claim 2 wherein the alkyl group is a 2-ethylhexyl group.

4. A process of claim 1 wherein R is a naphthyl group.

5. A process for producing 3,4-dichlorobutene-1 comprising the step of contacting 1,4-dichlorobutene-2 with a ferric carboxylate catalyst of the formula

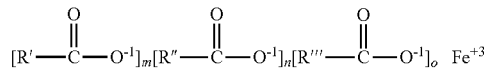

where R, R' and R" are independently alkyl or alkenyl groups of 4-18 carbon atoms, cycloalkyl or cycloalkenyl groups of 6-18 carbon atoms or aryl groups selected from phenyl, benzyl, xylyl, tolyl, and naphthyl groups, the sum of m, n and o is 3 and m, n and o are independently 0, 1 or 2, whereby a portion of the 1,4-dichlorobutene-2 is isomerized to form 3,4-dichlorobutene-1.

6. A process of claim 1 wherein the amount of catalyst present ranges from 0.01-1.0 weight percent, based on the weight of dichlorobutenes present.

7. A process for producing an equilibrium mixture of 3,4-dichlorobutene-1 and 1,4-dichlorobutene-2 comprising the step of contacting a dichlorobutene isomer selected from the group consisting of 1,4-dichlorobutene-2,3,4-dichlorobutene-1 and mixtures thereof with a ferric carboxylate catalyst of the formula

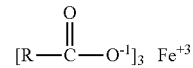

where R is an alkyl or alkenyl group of 4-18 carbon atoms, a cycloalkyl or cycloalkenyl group of 6-18 carbon atoms or an aryl group selected from phenyl, benzyl, xylyl, tolyl, and naphthyl groups.

* * * * *